United States Patent
Musa et al.

(10) Patent No.: US 7,326,746 B2
(45) Date of Patent: Feb. 5, 2008

(54) CURABLE ELECTRON DONOR COMPOSITIONS

(75) Inventors: Osama M. Musa, Hillsborough, NJ (US); Donald E. Herr, Flemington, NJ (US); Nikola A. Nikolic, Princeton, NJ (US)

(73) Assignee: National Starch and Chemical Investment Holding Corporation

( * ) Notice: Subject to any disclaimer, the term of this patent is extended or adjusted under 35 U.S.C. 154(b) by 405 days.

(21) Appl. No.: 10/967,493

(22) Filed: Feb. 17, 2005

(65) Prior Publication Data

US 2007/0060683 A1 Mar. 15, 2007

Related U.S. Application Data

(60) Division of application No. 09/922,187, filed on Aug. 3, 2001, now Pat. No. 6,908,957, which is a continuation of application No. 09/573,302, filed on May 18, 2000, now abandoned.

(51) Int. Cl.
*C08K 5/00* (2006.01)

(52) U.S. Cl. ............... 524/210; 524/211; 524/214; 524/216; 524/217; 524/218; 524/219; 524/220; 556/465; 556/482; 556/487; 556/489; 560/157; 564/17; 564/26; 564/30; 564/32; 564/47; 564/56

(58) Field of Classification Search ......... 524/210, 524/211, 214, 216, 217, 218, 219, 220
See application file for complete search history.

(56) References Cited

U.S. PATENT DOCUMENTS

| | | | |
|---|---|---|---|
| 4,401,777 A | 8/1983 | Tsuboi et al. | |
| 4,640,849 A | 2/1987 | Woods et al. | |
| 4,727,126 A | 2/1988 | Chen | |
| 4,732,956 A | 3/1988 | Woods et al. | |
| 4,883,883 A | 11/1989 | Barthelemy et al. | |
| 5,021,487 A | 6/1991 | Klemarczyk | |
| 6,034,195 A | 3/2000 | Dershem et al. | |

FOREIGN PATENT DOCUMENTS

| | | |
|---|---|---|
| DE | 2064 305 | 7/1972 |
| EP | 0 368 634 | 5/1990 |
| EP | 371 640 | 6/1990 |
| JP | 60064958 | 4/1985 |
| JP | 06273930 | 9/1994 |

OTHER PUBLICATIONS

XP-002246916, Feb. 15, 1990.
XP-002246917, Jul. 22, 1993.
XP-002246918, Jul. 31, 1997.
XP-002246919, Oct. 25, 2001.
XP-002248160, Jul. 31, 1997.
XP-002246676, Nov. 9, 1998.
XP-002246677, Jul 11, 1989.
XP-002246678, May 11, 1995.
XP-002246679, Feb. 3, 1995.
XP-002246680, Jun. 29, 1989.
XP-002246681, Jul. 5, 1989.
XP-002246682, Jun. 27, 1988.
XP-002246683, Jul. 11, 1989.
XP-002246684, Jun. 29, 1989.
XP-002246685, Feb. 15, 1990.
XP-002246686, Jun. 29, 1989.
XP-002246687, Feb. 15, 1990.
XP-002246688, Jul. 11, 1989.
XP-002246689, Feb. 15, 1990.
XP-002246690, Apr. 28, 1997.
XP-002246691, Feb. 16, 1990.
XP-002246913, Jul. 5, 1989.
XP-002246914, Jul. 5, 1989.
XP-002246915, Nov. 30, 1988.

*Primary Examiner*—Edward J. Cain
(74) *Attorney, Agent, or Firm*—Jane E. Gennaro

(57) ABSTRACT

Electron donor compounds, suitable for use as adhesives or as components in adhesives, contain a carbon to carbon double bond attached to an aromatic ring and conjugated with the unsaturation in the aromatic ring.

2 Claims, No Drawings

CURABLE ELECTRON DONOR COMPOSITIONS

This application is a divisional of application Ser. No. 09/922,187 filed Aug. 3, 2001, now U.S. Pat. No. 6,908,957 which is a continuation of application Ser. No. 09/573,302 filed May 18, 2000, now abandoned.

FIELD OF THE INVENTION

This invention relates to electron donor compounds and to curable adhesive compositions containing the electron donor compounds.

BACKGROUND OF THE INVENTION

Adhesive compositions, particularly conductive adhesives, are used for a variety of purposes in the fabrication and assembly of semiconductor packages and microelectronic devices. The more prominent uses are the bonding of integrated circuit chips to lead frames or other substrates, and the bonding of circuit packages or assemblies to printed wire boards.

There exist electron acceptor/donor adhesives for use in low modulus adhesives, particularly in fast-cure adhesives for chip attach applications, in which vinyl ethers are the electron donors. However, the number of suitable vinyl ethers as donors is limited due to their low boiling points, high volatility, and difficult preparations. Thus, there is a need for the development of new electron donors suitable for use in adhesives applications.

SUMMARY OF THE INVENTION

This invention relates to electron donor compounds comprising an electron donor group attached to a molecular (small molecule) or polymeric group. The electron donor is a carbon to carbon double bond connected to an aromatic ring and conjugated with the unsaturation in the aromatic ring.

The presence of electron donating substituents on the aromatic ring will increase the electron density on the carbon to carbon double bond, leading to higher reactivity. The reactivity will also be affected by steric interaction. An increase in the number of alkyl substituents on the carbon to carbon double bond will decrease the reactivity; preferably, all substituents on the carbon to carbon double bond will be hydrogen, or will be hydrogen with a methyl group as the only other substituent.

The electron donor is linked to the molecular or polymeric group through a linking group that is the product of the reaction between a functionality on the electron donor and a co-reactive functionality on the molecular or polymeric group. Alternatively, the electron donor group may be attached to the molecular or polymeric group through a coupling reaction in which the carbon to carbon double bond external to the aromatic ring (of the electron donor) is formed during the reaction.

The molecular or polymeric group may be a branched or linear alkane (with cyclic moieties), a siloxane, polysiloxane, a $C_1$ to $C_4$ alkoxy-terminated siloxane or polysiloxane, a polyether, a polyester, a polyurethane, a poly(butadiene), or an aromatic, polyaromatic, or heteroaromatic group.

This invention is also a curable composition comprising one or more of the inventive electron donor compounds, and optionally a curing agent and one or more fillers.

This invention is also a curable composition comprising one or more of the inventive electron donor compounds and one or more copolymerizable electron acceptor compounds, and optionally a curing agent and one or more fillers. Suitable electron acceptor compounds for copolymerization are fumarates and maleates, for example, dioctyl maleate, dibutyl maleate, dioctyl fumarate, dibutyl fumarate. Resins or compounds containing acrylate and maleimide functionality are other suitable electron acceptor materials.

DETAILED DESCRIPTION OF THE INVENTION

The electron donor compounds of this invention will have one of the structures depicted here:

Structure I:

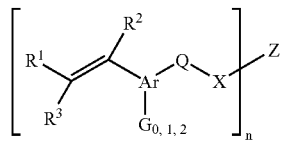

Structure II:

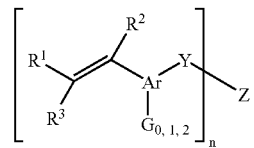

Structure III:

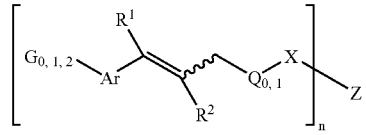

in which n is 1 to 6;

Ar is an aromatic or heteroaromatic ring or fused ring having 3 to 10 carbon atoms within the ring structure, in which the heteroatoms may be N, O, or S;

$R^1$, $R^2$, and $R^3$ are independently hydrogen, an alkyl group having 1 to 12 carbon atoms, or Ar as described above; preferably, $R^1$, $R^2$, and $R^3$ are hydrogen or an alkyl group having 1 to 4 carbon atoms, and more preferably are all hydrogen;

G is —$OR^4$, —$SR^4$, —$N(R^1)(R^2)$, Ar as described above, or an alkyl group having 1 to 12 carbon atoms, in which $R^1$ and $R^2$ are as described above and $R^4$ is Ar as described above or an alkyl group having 1 to 12 carbon atoms, preferably 1 to 4 carbon atoms;

Q is an alkyl group having 1 to 12 carbon atoms;

X is

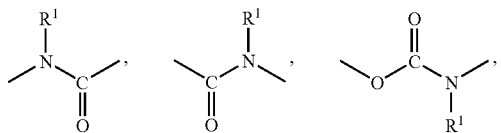

-continued

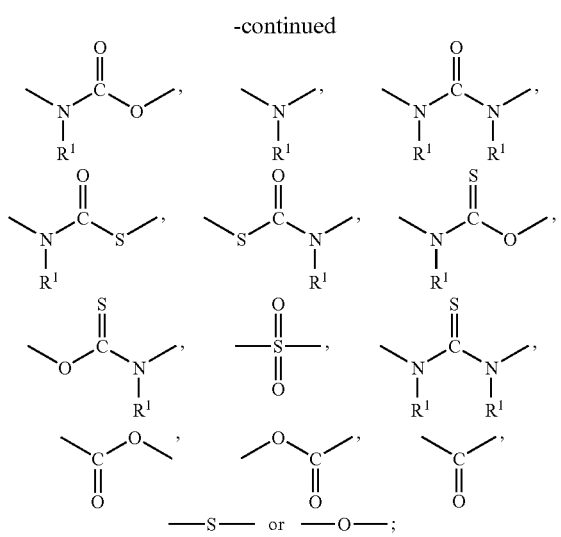

Y is

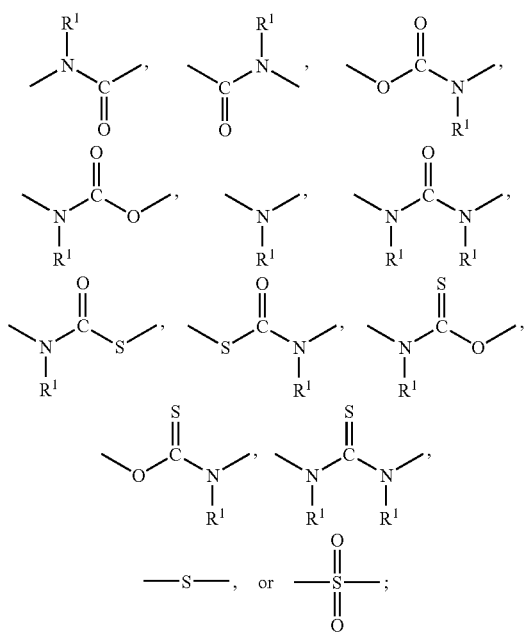

Z is an alkyl group, a siloxane, a polysiloxane, a $C_1$ to $C_4$ alkoxy-terminated siloxane or polysiloxane, a polyether, a polyester, a polyurethane, a poly(butadiene) or an aromatic, polyaromatic, or heteroaromatic group. Starting materials for preparation as the Z group are commercially available from a number of sources; for example, aromatic and polyaromatic materials may be obtained from BASF or Bayer; siloxanes and polysiloxanes from Gelest; polyethers from BASF; polyesters from Uniqema or Bayer; poly(butadiene)s from Elf-Atochem; polyurethanes from Bayer or BASF; and the branched or linear alkanes from Uniqema. Some of these sources will have available Z materials already functionalized for reaction with a co-reactive functionality on the electron donor; in other cases, the practitioner will need to functionalize the materials in preparation for reaction with the electron donor starting material.

The Z groups may contain cyclic moieties or heteroatoms, and may contain pendant hydroxyl or thiol groups depending on the synthetic route for making the electron donor compound; for example, if one of the starting compounds contains a hydroxyl or thiol functionality that is reacted with an epoxy functionality, the Z group will contain a pendant hydroxyl or thiol group.

The exact composition or molecular weight of Z is not critical to the invention and can range widely depending on the requirements of the end use for the electron donor compound. The composition of Z can be chosen to give specific material properties in a final formulation, such as, rheological properties, hydrophilic or hydrophobic properties, toughness, strength, or flexibility. For example, a low level of crosslinking and free rotation about polymeric bonds will impart flexibility to a compound, and the presence of siloxane moieties will impart hydrophobicity and flexibility. The molecular weight and chain length will affect viscosity, the higher the molecular weight and the longer the chain length, the higher the viscosity.

As used in this specification, aromatic means a compound that meets the classical definition of an aromatic compound, that is, it contains cyclic clouds of delocalized π electrons above and below the plane of the molecule and the π clouds have a total of (4n+2) electrons.

These electron donor compounds can be prepared through standard addition or condensation reactions between a functionality on a starting material containing the electron donor group and a co-reactive functionality on a starting material containing the molecular or polymeric group, or through common coupling reactions such as the Wittig, Heck, or Stille reactions. For example, useful starting compounds for the electron donor moiety are cinnamyl alcohol or chloride and 3-isopropenyl-α,α-dimethylbenzyl isocyanate. Although one skilled in the art can devise suitable variations in reactions, the variations will be guided in practice by the commercial availability of starting materials or ease of synthetic routes.

Representative synthetic routes include:
1. the reaction of isocyanate functionality with (i) hydroxyl; or (ii) amine; or (iii) thiol functionality to create a carbamate, urea or thiocarbamate linkage, respectively;
2. the substitution of a halogen with (i) hydroxyl; or (ii) amine; or (iii) thiol functionality to create an ether, amine or thio-ether linkage, respectively;
3. the reaction of an epoxy functionality with (i) hydroxyl; or (ii) amine; or (iii) thiol functionality to create an ether, amine or thio-ether linkage, respectively.

The electron donor compounds can be blended with electron acceptor compounds, such as fumarates, maleates, acrylates, and maleimides, for co-polymerization to form cured adhesive compositions for use in a wide variety of applications. Suitable fumarates and maleates are, for example, dioctyl maleate, dibutyl maleate, dioctyl fumarate, dibutyl fumarate. Suitable acrylates are numerous and are commercially available, for example, from Sartomer. Suitable maleimides are prepared, for example, according to procedures described in U.S. Pat. Nos. 6,034,194 and 6,034,195 to Dershem.

The electron donor compounds can be formulated into adhesive, coating, potting or encapsulant compositions that are well suited for use in electronics applications. The formulations preferably will contain one or more curing agents and conductive or nonconductive fillers, and may also contain stabilizing compounds, adhesion promoters or coupling agents.

Exemplary curing agents are thermal initiators and photoinitiators present in the adhesive composition in an amount of 0.1% to 10%, preferably 0.1% to 3.0%, by weight of the electron donor compound. Preferred thermal initiators include peroxides, such as butyl peroctoates and dicumyl peroxide, and azo compounds, such as 2,2'-azobis(2-methyl-propanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable, for example, the curing process can be started by irradiation, and in a later processing step curing can be completed by the application of heat to accomplish the thermal cure.

In general, these compositions will cure within a temperature range of 70° C. to 250° C., and curing will be effected within a range of ten seconds to three hours. The time and temperature curing profile of each formulation will vary with the specific electron donor compound and the other components of the formulation, but the parameters of a curing profile can be determined by a practitioner skilled in the art without undue experimentation.

Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. When present, fillers will be in amounts of 20% to 90% by weight of the formulation.

Suitable adhesion promoters or coupling agents are silanes, silicate esters, metal acrylates or methacrylates, titanates, and compounds containing a chelating ligand, such as phosphine, mercaptan, and acetoacetate. When present, coupling agents will be in amounts up to 10% by weight, and preferably in amounts of 0.1% to 3.0% percent by weight of the electron donor compounds.

In addition, the formulations may contain compounds that lend additional flexibility and toughness to the resultant cured material. Such compounds may be any thermoset or thermoplastic material having a Tg of 150° C. or less, and typically will be a polymeric material, such as, a polyacrylate, poly(butadiene), polyTHF (polymerized tetrahydrofuran), carboxy-terminated butyronitrile rubber and polypropylene glycol. When present, these compounds may be in an amount up to about 15% by weight of the electron donor compound.

EXAMPLES

The following examples show representative electron donor compounds and reactions for their preparation. The electron donor reaction products were characterized by $^1$H-NMR and FT-IR. The examples are illustrative of the invention and are not intended as a limitation.

In these examples, fnc-$C_{36}$-fnc represents a mixture of isomers resulting from the dimerization of oleic and linoleic acids followed by conversion to the appropriate functionality in which fnc is —OH for alcohols, —NH$_2$ for amines, and —NCO for isocyanates;

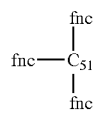

represents a mixture of isomers resulting from the trimerization of oleic and linoleic acids followed by conversion to the appropriate functionality in which fnc is —COOH for carboxyl groups, —CH$_2$OH for alcohols; and $C_{36}$ within a compound represents a mixture of isomers of linear and branched chain alkyls having 36 carbon atoms, which is the residue of the dimer or trimer acid in the compound, after the exemplified reaction.

Example 1

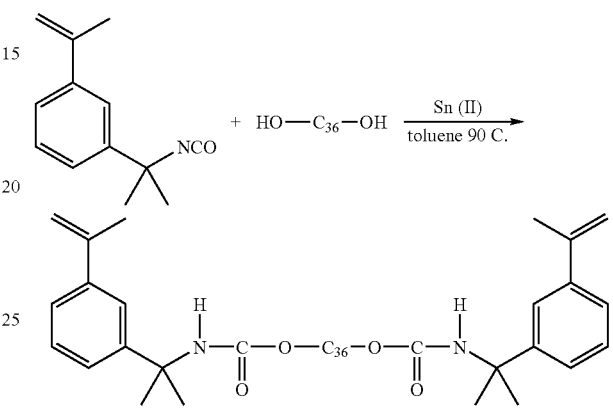

3-Isopropenyl-α,α-dimethylbenzyl isocyanate (m-TMI) (35.6 g, 0.177 mole) was solvated in toluene (100 g) in a 500 Ml three-necked flask equipped with a mechanical stirrer, addition funnel and nitrogen inlet/outlet. The reaction was placed under nitrogen, and 0.033 g of dibutyltin dilaurate (catalyst) was added with stirring as the solution was heated to 90° C. The addition funnel was charged with HO—C$_{36}$—OH (50.12 g, 0.0884 mole) (Pripol 2033, Uniqema) dissolved in toluene (50 g). This solution was added to the isocyanate solution over ten minutes, and the resulting mixture heated for an additional three hours at 90° C. After the reaction was allowed to cool to room temperature, the mixture was washed with distilled water three times. The isolated organic layer was dried over MgSO$_4$, filtered and the solvent removed in vacuo to give the product in 93% yield.

Example 2

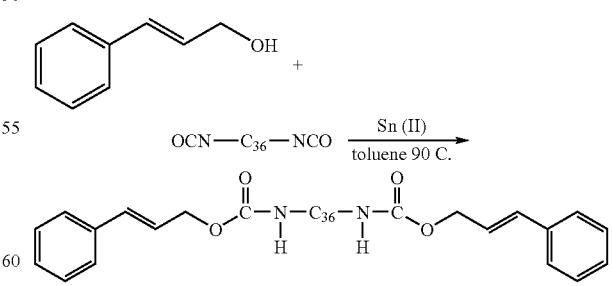

OCN—C$_{36}$—NCO (DDI 1410, Henkel) (98.79 g, 0.164 mole) was solvated in toluene (100 g) in a 500 mL three-necked flask equipped with a mechanical stirrer, addition funnel and nitrogen inlet/outlet. The reaction was placed under nitrogen, and 0.04 g of dibutyltin dilaurate (catalyst)

was added with stirring as the solution was heated to 90° C. The addition funnel was charged with cinnamyl alcohol (44.01 g, 0.328 mole) dissolved in toluene (50 g). This solution was added to the isocyanate solution over ten minutes, and the resulting mixture was heated for an additional three hours at 90° C. After the reaction was allowed to cool to room temperature, the mixture was washed with distilled water three times. The isolated organic layer was dried over $MgSO_4$, filtered and the solvent removed in vacuo to give the product in 94% yield.

Example 3

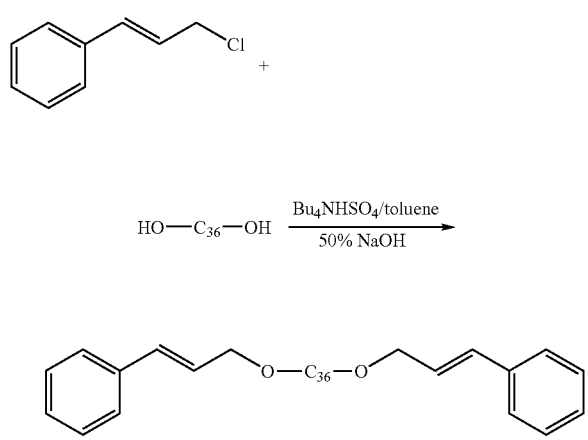

HO—$C_{36}$—OH (Pripol 2033, Uniqema) (54.36 g, 0.096 mole), 50% NaOH (400 mL), tetrabutyl ammonium hydrogen sulfate (13.8 g, 0.041 mole), and cinnamyl chloride (33.69 g, 0.221 mole) in toluene were stirred for five hours at 53° C., then for 15 hours at 75° C. The reaction was allowed to cool to room temperature and the organic layer extracted and washed with brine three times. The isolated organic layer was dried over $MgSO_4$, filtered and the solvent removed in vacuo to give the product in 95% yield.

Example 4

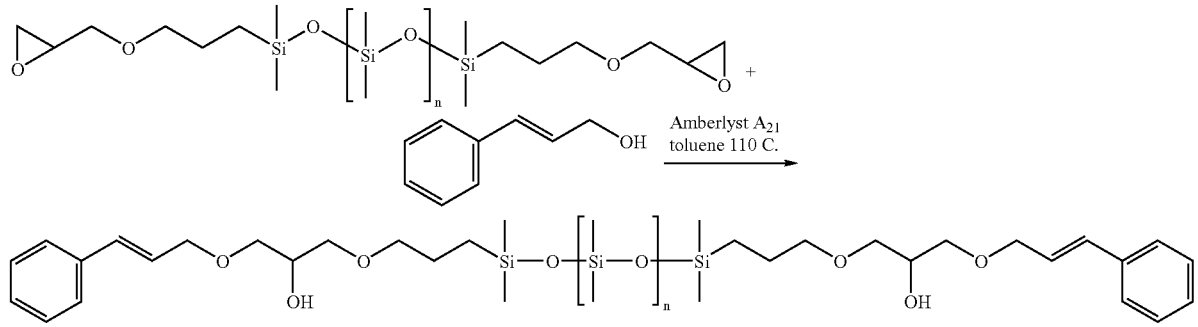

where n is 9.

Epoxypropoxypropyl terminated polydimethylsiloxanes (DMS-E12, Gelest Inc.) (10 g, 0.01 mole), cinnamyl alcohol (2.68 g, 0.02 mole) and an ion exchange resin (2 g) (Amberlyst A-21) were heated together at 110° C. for 20 hours. The ion exchange resin was separated from the reaction mixture to give the product in 94% yield.

Example 5

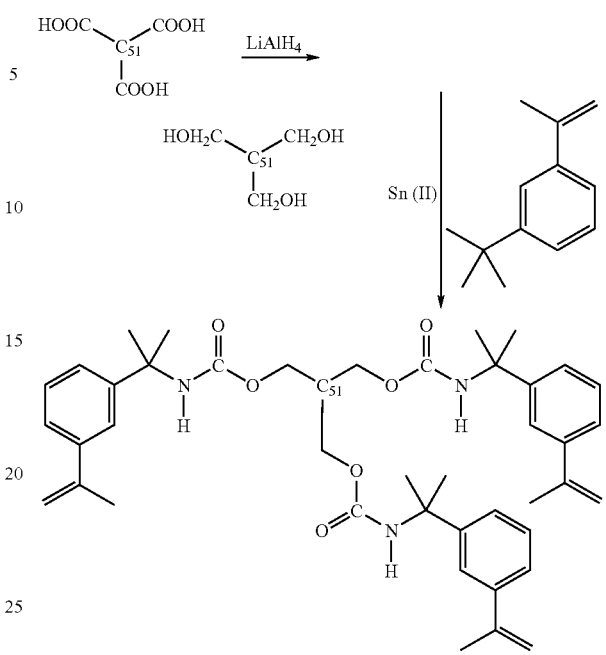

A suspension of $LiAlH_4$ (0.84 g, 0.022 mole) and ether (100 mL) in a dry 500 mL three-necked round-bottom flask equipped with a reflux condenser under nitrogen was cooled to 0° C. To this was added slowly trimer triacid (10 g, 0.011 mole) in ether (50 mL). The reaction mixture was stirred at room temperature for five minutes. Water was added (100 mL) and the salt was removed by filtration. The organic layer was separated and dried over $MgSO_4$. The solvent was removed under reduced pressure to give the trimer triol.

3-Isopropenyl-α,α-dimethylbenzyl isocyanate (m-TMI) (3.57 g, 0.018 mole) was solvated in toluene (100 mL) in a 500 mL three-necked flask equipped with a mechanical stirrer, addition funnel and nitrogen inlet/outlet. The reaction was placed under nitrogen, and dibutyltin dilaurate (0.001 g) was added with stirring as the solution heated to 90° C. The addition funnel was charged with the trimer triol (5.1 g, 0.0059 mole) dissolved in toluene (50 mL). This solution was added to the isocyanate solution over 10 minutes, and the resulting mixture heated for an additional three hours at 90° C. After the reaction was allowed to cool to room temperature, the mixture was washed with distilled water three times. The isolated organic layer was dried over $MgSO_4$, filtered, and the solvent removed in vacuo to give the product in 95% yield.

Example 6

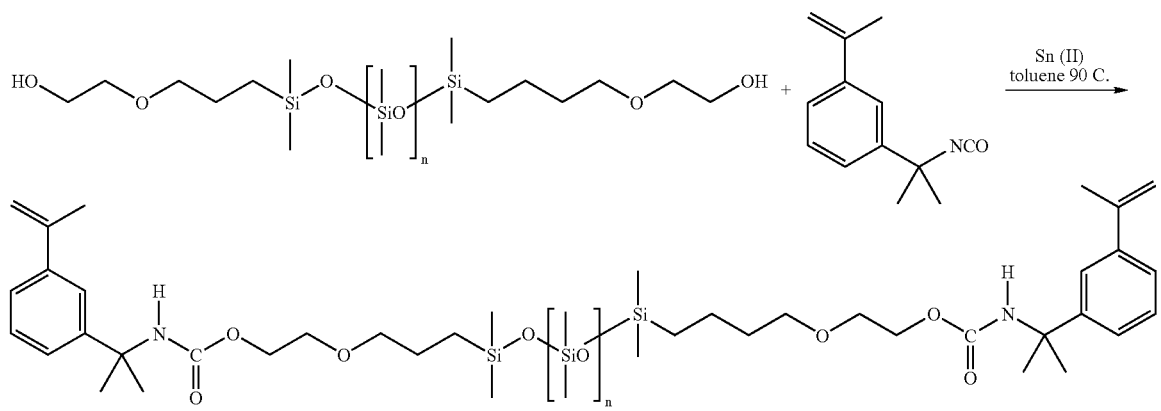

where n is 9.

3-Isopropenyl-α,α-dimethylbenzyl isocyanate (m-TMI) (8.05 g, 0.04 mole) was solvated in toluene (50 g) in a 250 mL three-necked flask equipped with a mechanical stirrer, addition funnel and nitrogen inlet/outlet. The reaction was placed under nitrogen, and dibutyltin dilaurate (0.003 g) was added with stirring as the solution heated to 90° C. The addition funnel was charged with carbinol (hydroxyl) terminated polydimethylsiloxane (DMS-C15 available from Gelest Inc.) (20 g, 0.04 mole) dissolved in toluene (25 g). This solution was added to the isocyanate solution over ten minutes, and the resulting mixture heated for an additional three hours at 90° C. After the reaction was allowed to cool to room temperature, the mixture was washed with distilled water three times. The isolated organic layer was dried over MgSO₄, filtered and the solvent removed in vacuo to give the product in 95% yield.

Example 7

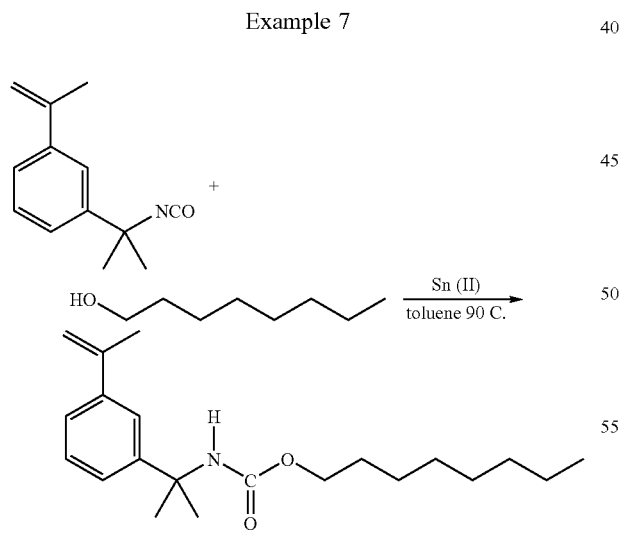

3-Isopropenyl-α,α-dimethylbenzyl isocyanate (m-TMI) (10 g, 0.05 mole) was solvated in toluene (50 g) in a 250 mL three-necked flask equipped with a mechanical stirrer, addition funnel and nitrogen inlet/outlet. The reaction was placed under nitrogen, and dibutyltin dilaurate (0.003 g) was added with stirring as the solution was heated to 90 C. The addition funnel was charged with 1-octanol (6.47 g, 0.05 mole) dissolved in toluene (25 g). This solution was added to the isocyanate solution over ten minutes, and the resulting mixture heated for an additional three hours at 90° C. After the reaction was allowed to cool to room temperature, the mixture was washed with distilled water three times. The isolated organic layer was dried over MgSO₄, filtered and the solvent removed in vacuo to give the product in 97% yield.

Using the same procedure, a branched chain alcohol with 18 or 24 carbons can be substituted. The alcohols are commercially available from Uniqema and Jarchem. In the structures below $C_{18}$ and $C_{24}$ represent a branched chain alkyl group with 18 or 24 carbons, respectively.

Example 8

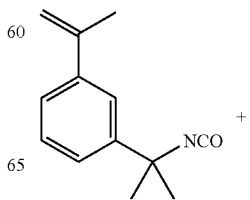

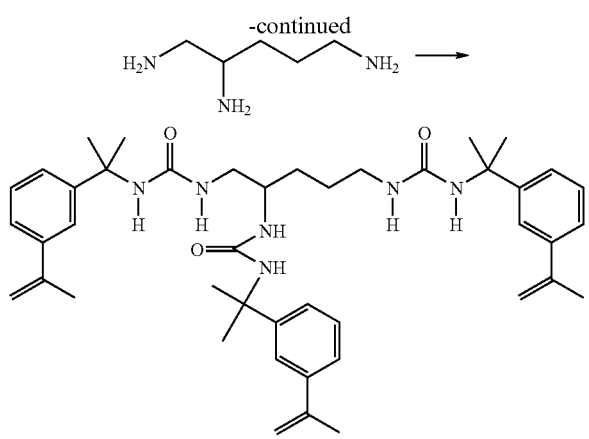

Three molar equivalents of 3-isopropenyl-α,α-dimethylbenzyl isocyanate (m-TMI) are solvated in toluene in a three-necked flask equipped with a mechanical stirrer, addition funnel and nitrogen inlet/outlet. The reaction is placed under nitrogen. The addition funnel is charged with one equivalent amount of tri-functional amine (three molar equivalents of amine functionality) dissolved in toluene. This solution is added to the isocyanate solution over ten minutes and the resulting mixture heated for three hours at 90° C. After the reaction is allowed to cool to room temperature, the mixture is washed with distilled water three times. The isolated organic layer is dried over MgSO$_4$, filtered and the solvent removed in vacuo to give the product.

Example 9

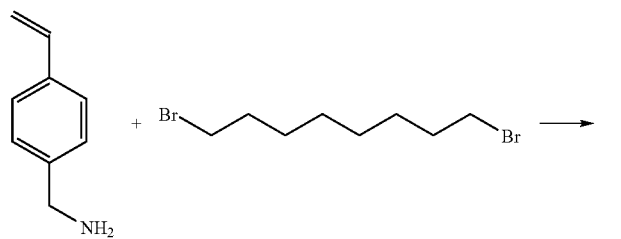

Two molar equivalents of 4-vinyl benzyl amine are solvated in THF in a three-necked flask equipped with a mechanical stirrer, addition funnel and nitrogen inlet/outlet. The reaction is placed under nitrogen. The addition funnel is charged with one molar equivalent of 1,8-dibromooctane dissolved in THF. This solution is added to the amine solution over ten minutes and the resulting mixture heated for three hours at 60° C. After the reaction is allowed to cool to room temperature, the THF is removed under reduced pressure, and the residue is partitioned between ether and water. The organic layer is separated, dried over MgSO4, filtered, and the solvent is removed under reduced pressure to give the product.

Example 10

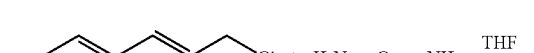

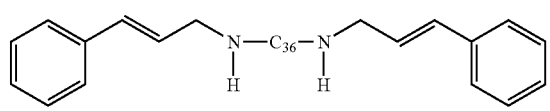

One equivalent of H$_2$N—C$_{36}$—NH$_2$ (Versamine 552, Henkel) is solvated in THF in a three-necked flask equipped with a mechanical stirrer, addition funnel and nitrogen inlet/outlet. The reaction is placed under nitrogen. The addition funnel is charged with two equivalents of cinnamyl chloride dissolved in THF. This solution is added to the H$_2$N—C$_{36}$—NH$_2$ solution over ten minutes and the resulting mixture heated for three hours at 60° C. After the reaction is allowed to cool to room temperature, the THF is removed under reduced pressure, and the residue is partitioned between ether and water. The organic layer is separated, dried over MgSO4, filtered and the solvent is removed under reduced pressure to give the product in 90% yield.

Example 11

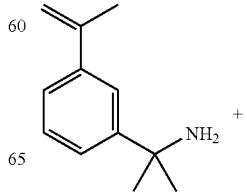

-continued

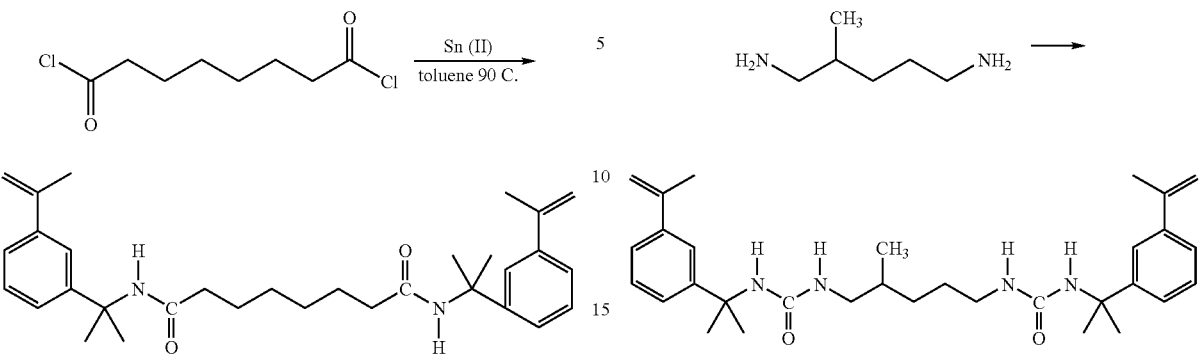

One equivalent of suberoyl chloride is solvated in toluene in a three-necked flask equipped with a mechanical stirrer, addition funnel and nitrogen inlet/outlet. The reaction is placed under nitrogen. The addition funnel is charged with two equivalents of 3-isopropenyl-α,α-dimethylbenzyl amine and one equivalent of triethyl amine dissolved in THF. This solution is added to the suberoyl chloride solution over five minutes and the resulting mixture heated for three hours at 70° C. After the reaction is allowed to cool to room temperature, the mixture is washed with distilled water three times. The isolated organic layer is dried over $MgSO_4$, filtered and the solvent removed in vacuo to give the product in 91% yield.

Example 12

Two equivalents of 3-isopropenyl-α,α-dimethylbenzyl isocyanate (m-TMI) is solvated in toluene in a three-necked flask equipped with a mechanical stirrer, addition funnel and nitrogen inlet/outlet. The reaction is placed under nitrogen. The addition funnel is charged with one equivalent of 2-methyl-pentane diamine, DYTEK A, dissolved in toluene. This solution is added to the isocyanate solution over ten minutes and the resulting mixture heated for three hours at 90° C. After the reaction is allowed to cool to room temperature, the mixture is washed with distilled water three times. The isolated organic layer is dried over $MgSO_4$, filtered and the solvent removed in vacuo to give the product.

Example 13

Other electron donor compounds can be made according to similar procedures. The following reaction schemes show other aromatic ring starting compounds and reactant organic compounds with the resulting electron donor compounds.

Example 13-A

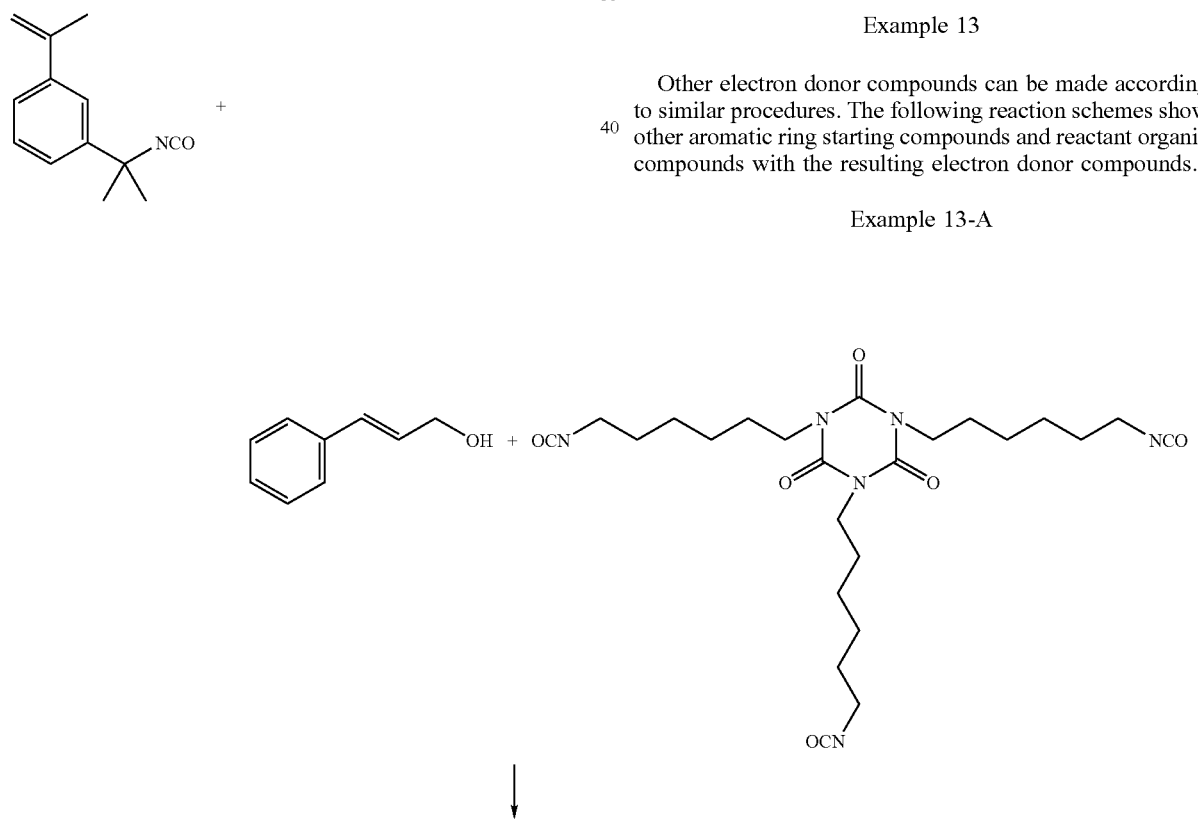

-continued
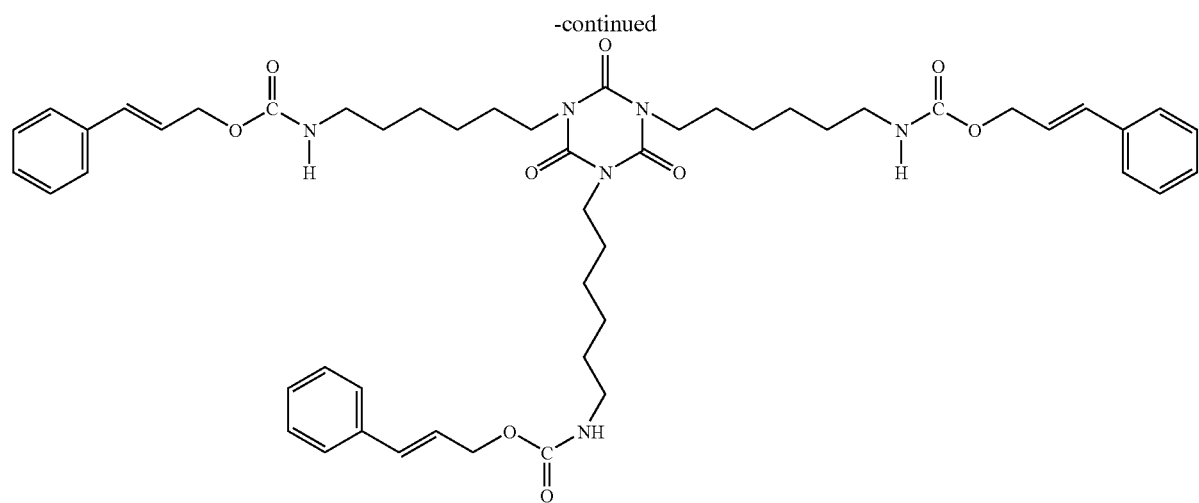
Example 13-B
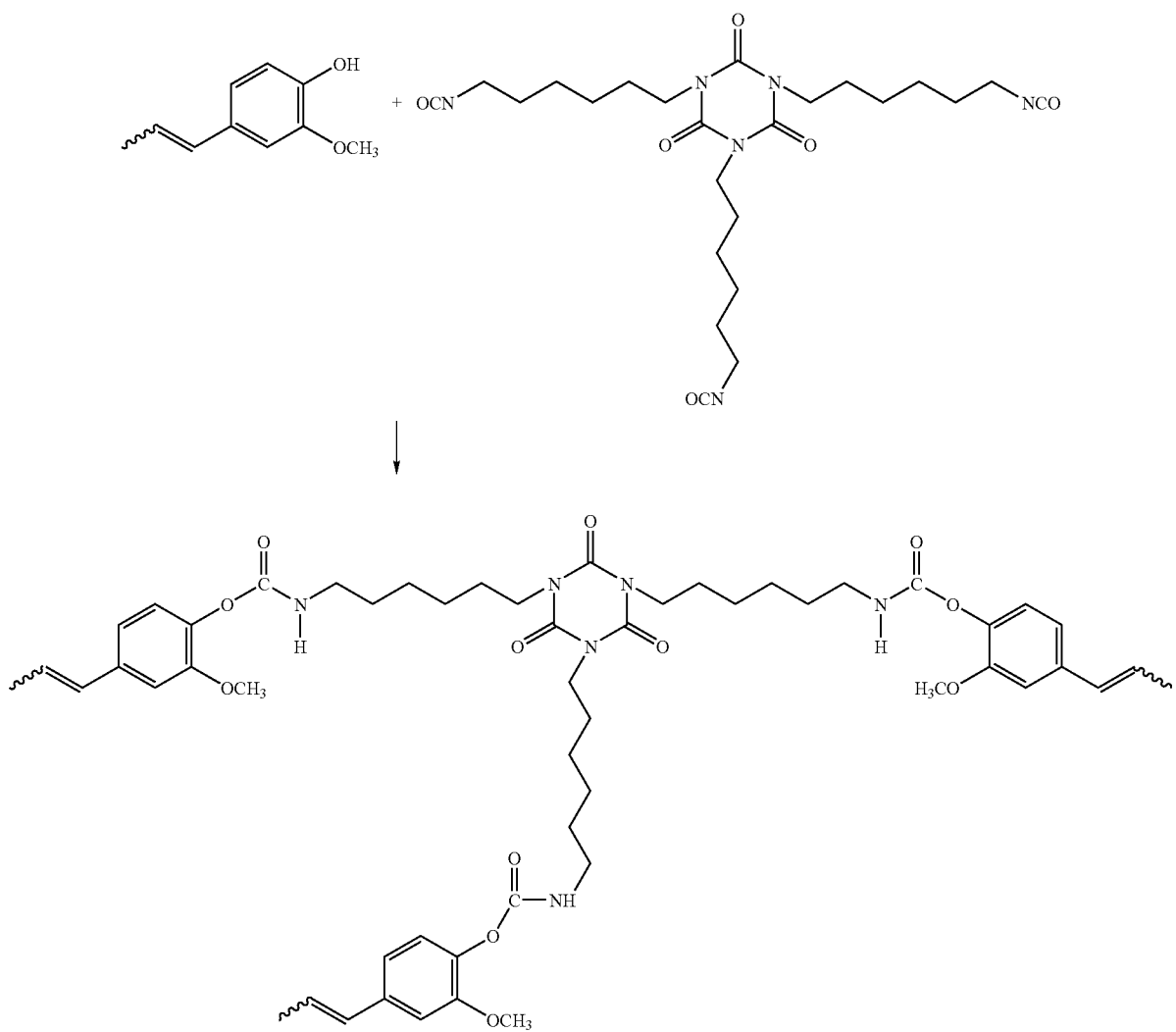

17
Example 13-C
18
Example 13-D
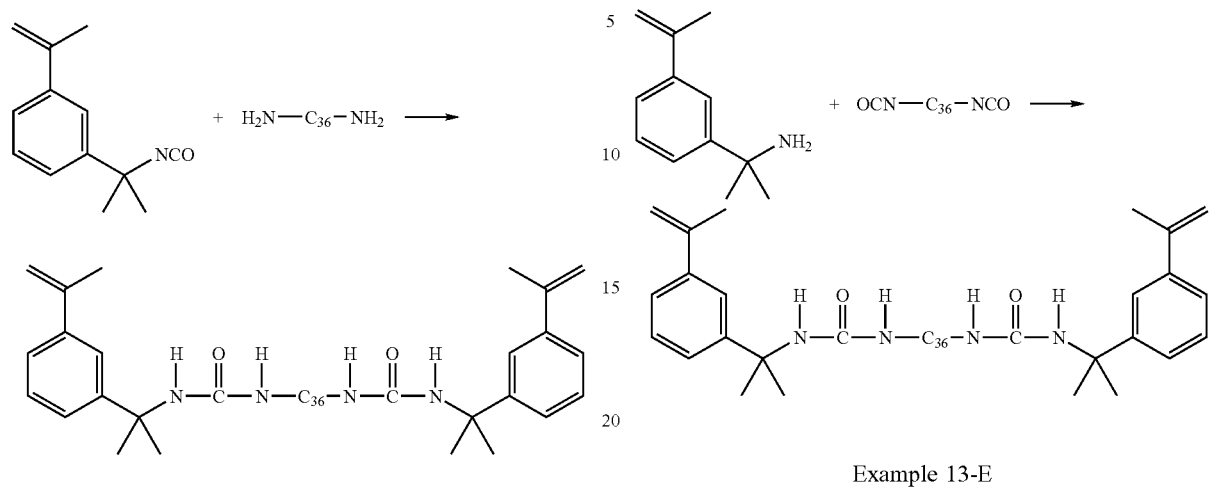
Example 13-E
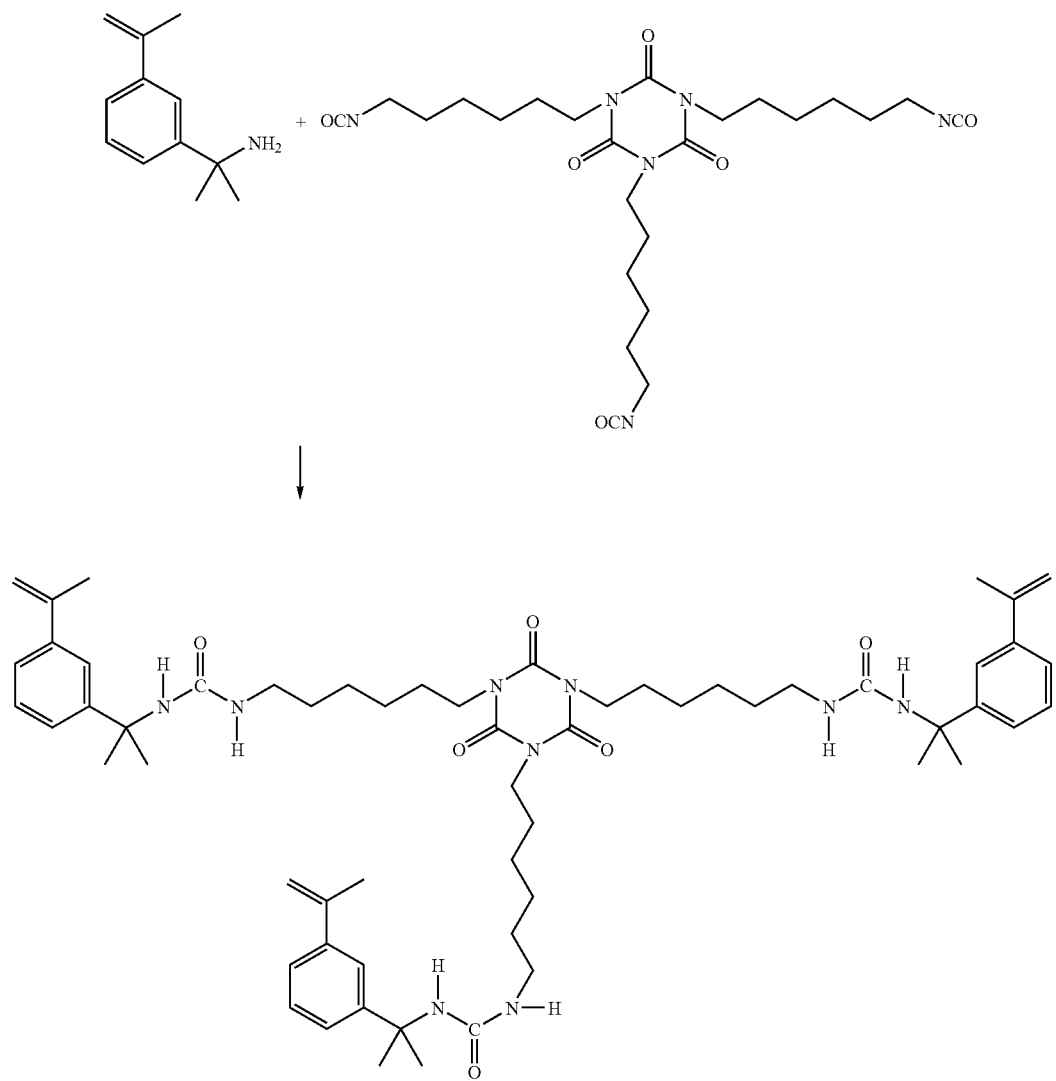

19
Example 13-F
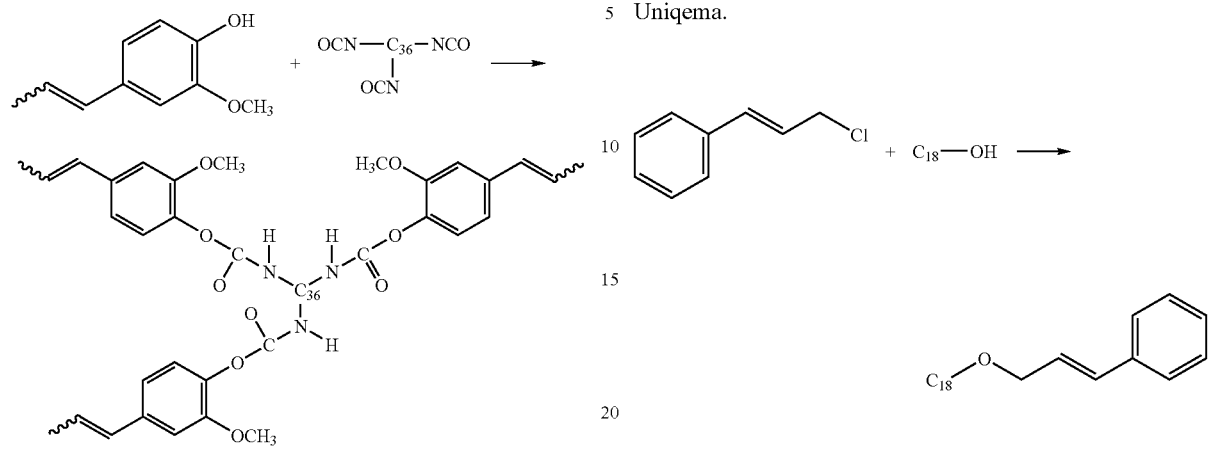
Example 13-H
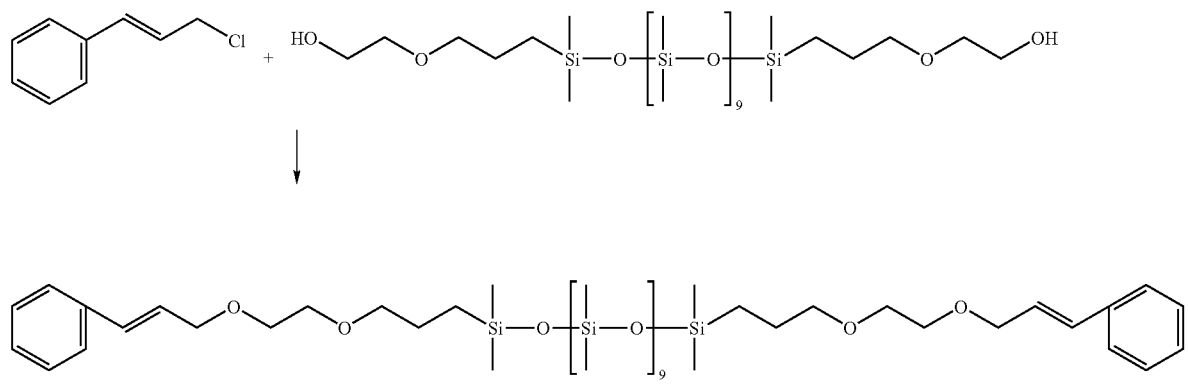
20
Example 13-G
In this example $C_{18}$—OH represents an 18 carbon branched chain alcohol commercially available from Uniqema.
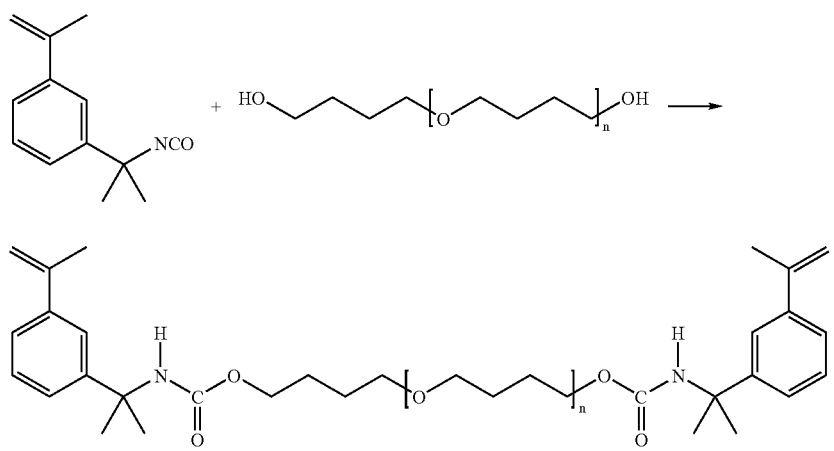
Example 13-I
In these structures, n is an integer representing the number of times the unit in brackets is repeated. This can be varied by choice of commercially available materials.

Example 13-J

In these structures, n is an integer representing the number of times the unit in brackets is repeated. This can be varied by choice of commercially available materials.

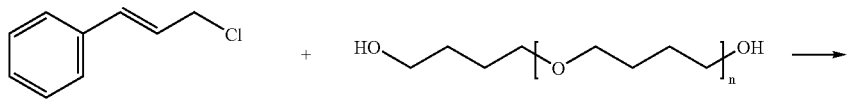

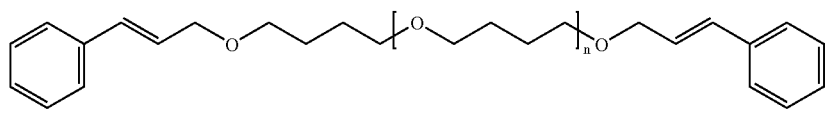

Example 13-K

Example 13-L

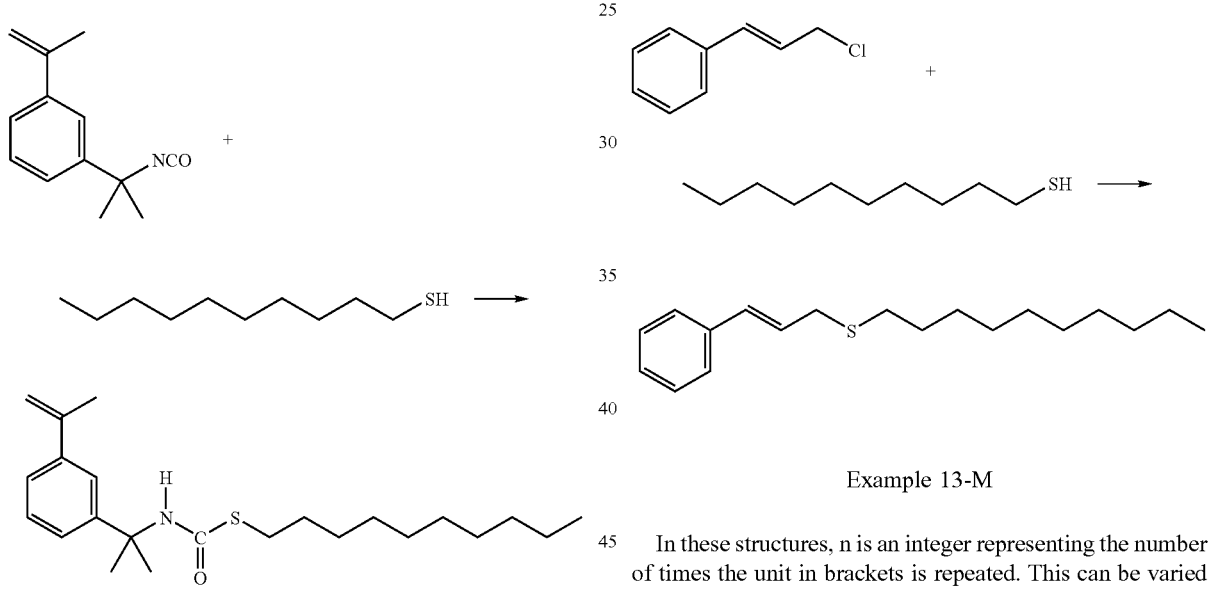

Example 13-M

In these structures, n is an integer representing the number of times the unit in brackets is repeated. This can be varied by choice of commercially available materials.

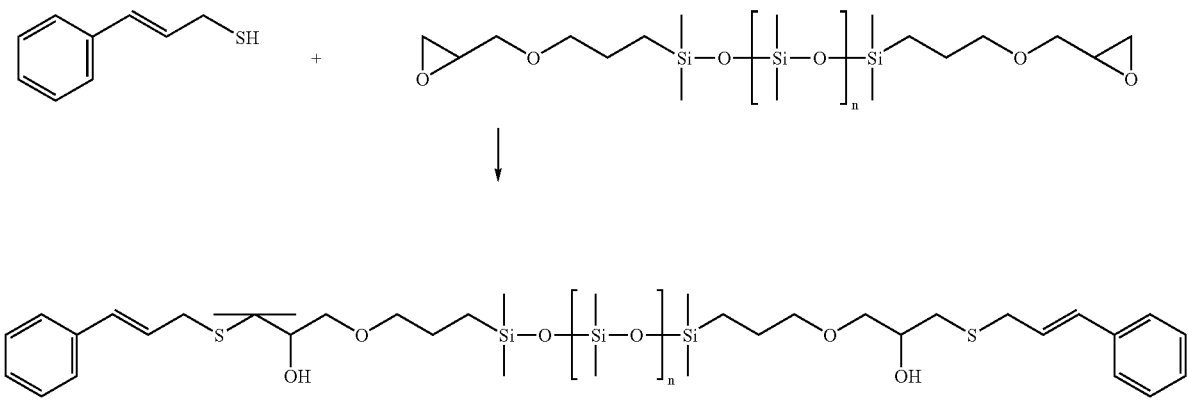

Example 13-N
In these structures, n is an integer representing the number of times the unit in brackets is repeated. This can be varied by choice of commercially available materials.
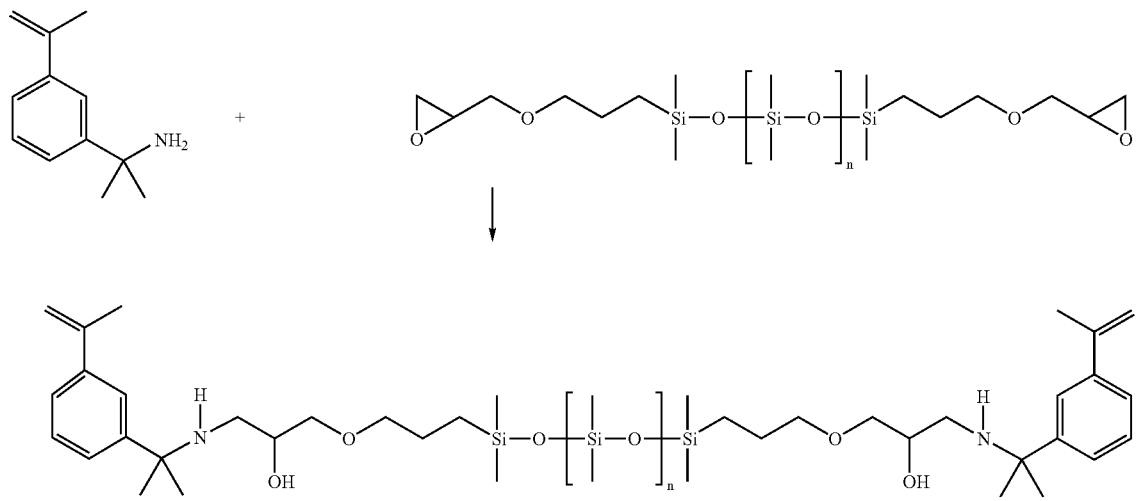
Example 13-O
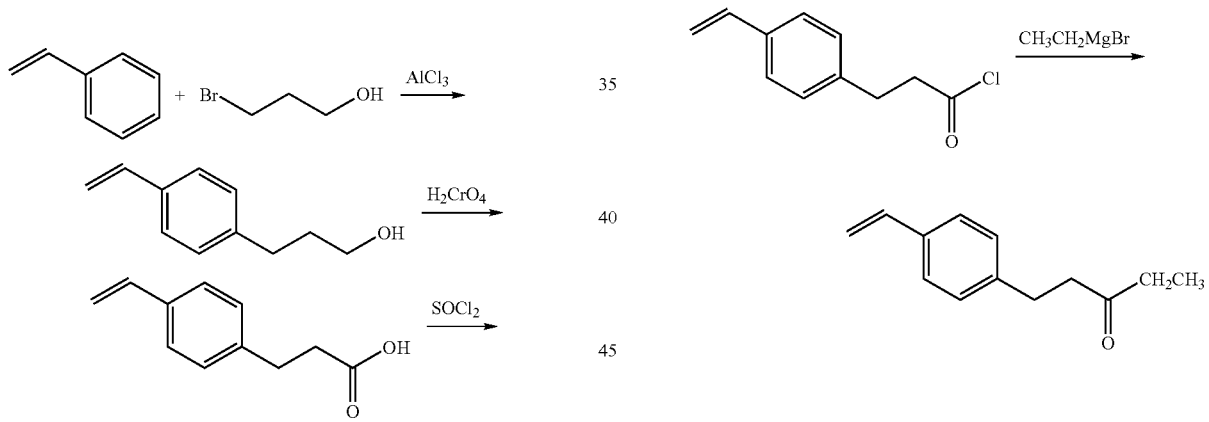
Example 13-P
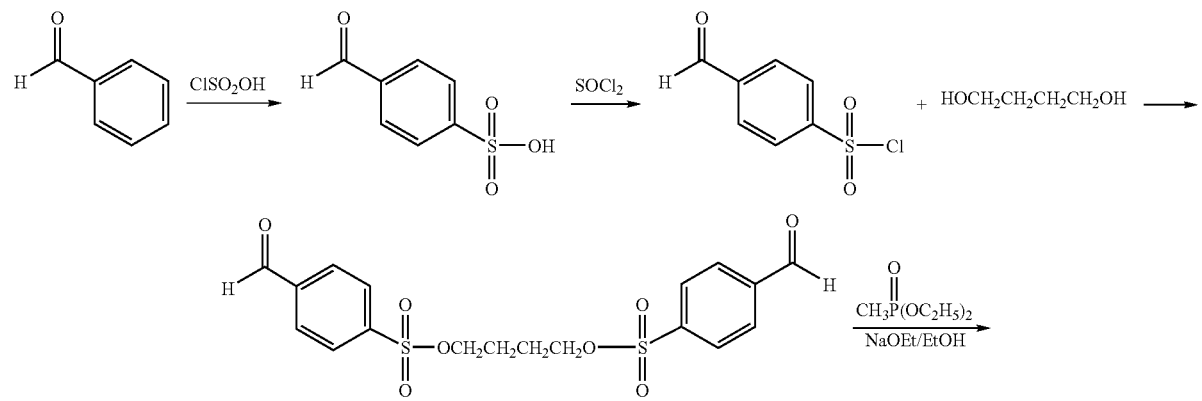

-continued

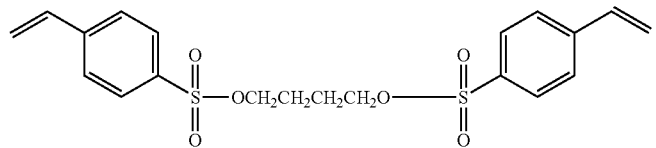

Example 13-Q

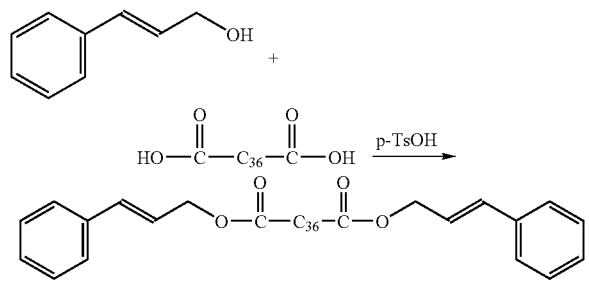

where p-TsOH is para-toluene sulfonic acid.

Example 14

Adhesive Formulations

Three of the electron donor compounds from the previous examples were formulated into adhesive compositions using a bismaleimide as the electron acceptor. The bismaleimide was derived from amino-terminated polyoxy-butylene (Versalink P650, Air Products) and maleic anhydride according to the procedures outlined in U.S. Pat. No. 4,745,197, using USP-MD (Witco Corporation) as an initiator.

The adhesive compositions were cured (copolymerization of the electron donor and the electron acceptor) using DSC. Exotherms for each of these resins appeared to be qualitatively similar in peak, and in peak to onset characteristics.

The formulations also were tested for use as die-attach adhesives for use in microelectronic devices: formulations were placed between a Pd lead frame and a 120×120 mil silicon die and cured on a hot plate at 200° C. for about 60 seconds. Pressure was applied to the side of the die at room temperature until shearing occurred. The die-shear force was measured in Kg. The results are included in the following formulation tables and show die shear values within a commercially usable range.

| Formulation 1 | | |
| --- | --- | --- |
| Component | Mass (g) | Weight % |
| BisMaleimide (Versalink P650) (electron acceptor) | 0.54 | 11.19 |
| TMI/dimer diol bis-carbamate (example 1) | 0.50 | 10.31 |
| Maleic anhydride 8% (Ricon 131) (reactive diluent) | 0.121 | 2.50 |
| Initiator | 0.024 | 0.50 |
| Blend of adhesion promoters | 0.0242 | 0.50 |
| Silver Flakes | 3.69 | 75.0 |
| RT Die Shear 13.9 Kg | | |

| Formulation 2 | | |
| --- | --- | --- |
| Component | Mass (g) | Weight % |
| Bismaleimide (Versalink P650) (electron acceptor) | 0.56 | 11.15 |
| Cinnamyl alcohol/dimer diisocyanate bis carbamate. (example 2) | 0.52 | 10.35 |
| Maleic anhydride 8% (Ricon 131) (reactive diluent) | 0.126 | 2.50 |
| Initiator | 0.0252 | 0.50 |
| Blend of adhesion promoters | 0.0252 | 0.50 |
| Silver Flake | 3.78 | 75.0 |
| RT Die Shear 6.1 Kg | | |

| Formulation 3 | | |
| --- | --- | --- |
| Component | Mass (g) | Weight % |
| Bismaleimide (Versalink P650 BMI) (electron acceptor) | 0.49 | 10.66% |
| m-TMI/trimer triol tris-carbamate (example 5) | 0.50 | 10.84% |
| Maleic anhydride 8% (reactive diluent) | 0.115 | 2.50% |
| Initiator | 0.0231 | 0.50% |
| Blend of adhesion promoters | 0.023 | 0.50% |
| Silver Flake | 3.46 | 75% |
| RT Die Shear 15.8 Kg | | |

A further advantage of the electron donor compounds is the fact that the addition of a minor amount to an adhesive formulation containing a vinyl ether will prevent the adhesive composition from dispersing or bleeding when applied to a low energy substrate.

What is claimed is:

1. A composition comprising a conductive or non-conductive filler and a compound having the structure:

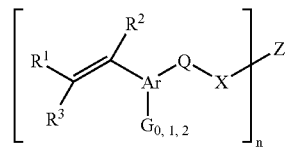

in which n is 1;

Ar is an aromatic or heteroaromatic ring or fused ring having 3 to 10 carbon atoms within the ring structure, in which the heteroatoms may be N, O, or S;

$R^1$, $R^2$, and $R^3$ are independently hydrogen, an alkyl group having 1 to 12 carbon atoms, or Ar as described above;

G is —$OR^4$, —$SR^4$, —$N(R^1)(R^2)$, Ar as described above, or an alkyl group having 1 to 12 carbon atoms, in which R[1] and R[2] are as described above and R[4] is Ar as described above or an alkyl group having 1 to 12 carbon atoms;

Q is an alkyl group having 1 to 12 carbon atoms;

X is

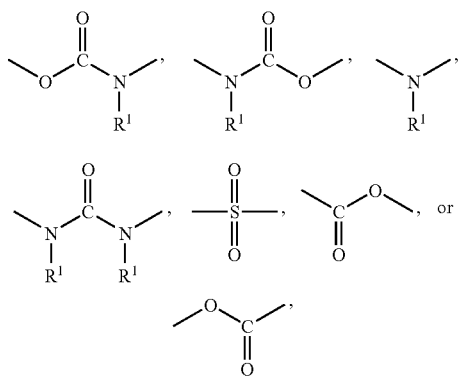

and Z is an alkyl group, a siloxane, a polysiloxane, a $C_1$ to $C_4$ alkoxy-terminated siloxane or polysiloxane, a polyether, a polyester, a polyurethane, a poly(butadiene), or an aromatic, polyaromatic or heteroaromatic group.

2. A composition comprising a conductive or non-conductive filler and a compound having the structure:

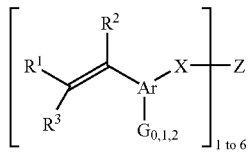

in which

Ar is an aromatic or heteroaromatic ring or fused ring having 3 to 10 carbon atoms within the ring structure, in which the heteroatoms may be N, O, or S;

R[1], R[2], and R[3] are independently hydrogen, an alkyl group having 1 to 12 carbon atoms, or Ar as described above;

G is —OR[4], —SR[4], —N(R[1])(R[2]), Ar as described above, or an alkyl group having 1 to 12 carbon atoms, in which R[1] and R[2] are as described above and R[4] is Ar as described above or an alkyl group having 1 to 12 carbon atoms;

X is

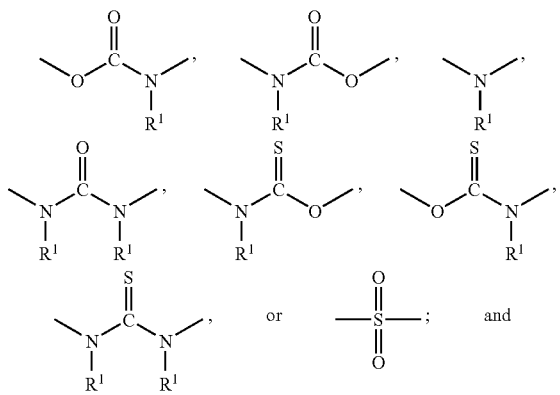

Z is an alkyl group, a siloxane, a polysiloxane, a $C_1$ to $C_4$ alkoxy-terminated siloxane or polysiloxane, a polyether, a polyester, a polyurethane, a poly(butadiene), or an aromatic, polyaromatic or heteroaromatic group.

* * * * *